(12) United States Patent
Lee et al.

(10) Patent No.: US 10,456,317 B2
(45) Date of Patent: Oct. 29, 2019

(54) SYSTEM AND METHOD FOR CONTROLLING JOINT ANGLE OF KNEE-JOINT TYPE WALKING TRAINING ROBOT

(71) Applicant: KOREA POLYTECHNIC UNIVERSITY INDUSTRY ACADEMIC COOPERATION FOUNDATION, Siheung-si, Gyeonggi-do (KR)

(72) Inventors: Eung Hyuk Lee, Bucheon-si (KR); Su Hong Eom, Incheon (KR); Mun Suck Jang, Bucheon-si (KR); Won Young Lee, Jeollabuk-do (KR)

(73) Assignee: KOREA POLYTECHNIC UNIVERSITY INDUSTRY ACADEMIC COOPERATION FOUNDATION, Siheung-si, Gyeonggi-Do (KR)

( * ) Notice: Subject to any disclaimer, the term of this patent is extended or adjusted under 35 U.S.C. 154(b) by 708 days.

(21) Appl. No.: 15/103,573

(22) PCT Filed: Nov. 19, 2014

(86) PCT No.: PCT/KR2014/011114
§ 371 (c)(1),
(2) Date: Jun. 10, 2016

(87) PCT Pub. No.: WO2015/099292
PCT Pub. Date: Jul. 2, 2015

(65) Prior Publication Data
US 2016/0310342 A1 Oct. 27, 2016

(30) Foreign Application Priority Data
Dec. 27, 2013 (KR) .................. 10-2013-0164956

(51) Int. Cl.
*A61H 3/00* (2006.01)
*A61H 1/02* (2006.01)
(Continued)

(52) U.S. Cl.
CPC ............ *A61H 3/00* (2013.01); *A61B 5/1038* (2013.01); *A61B 5/1121* (2013.01); *A61H 1/024* (2013.01);
(Continued)

(58) Field of Classification Search
CPC ......... A61H 3/00; A61H 1/024; A61B 5/1038
See application file for complete search history.

(56) References Cited

FOREIGN PATENT DOCUMENTS

| JP | 2010-099418 A | 5/2010 |
|---|---|---|
| JP | 2011-200363 A | 10/2011 |

(Continued)

*Primary Examiner* — Jason-Dennis N Stewart
(74) *Attorney, Agent, or Firm* — Novick, Kim & Lee, PLLC; Jae Youn Kim

(57) ABSTRACT

The present invention relates to a system and a method for controlling a joint angle of a knee-joint type walking training robot which estimates a walking stage of a person receiving rehabilitation for walking and actively responds to the walking stage on the basis thereof. The present invention can easily control the joint angle of the knee-joint type walking training robot by providing a configuration comprising: a pressure measuring device for measuring the pressure on the sole of a walker's foot by using a pressure sensor; and a joint angle estimating device for estimating the joint angle of a knee-joint by extracting movement time of the walk and the length of the part of the sole contacting the ground on the basis of the sole's pressure measured by the pressure measuring device.

9 Claims, 6 Drawing Sheets

(51) Int. Cl.
  *A61B 5/103*  (2006.01)
  *A61B 5/11*  (2006.01)
  *B25J 9/16*  (2006.01)

(52) U.S. Cl.
  CPC .............. *B25J 9/16* (2013.01); *B25J 9/1612* (2013.01); *A61H 2201/164* (2013.01); *A61H 2201/165* (2013.01); *A61H 2201/1642* (2013.01); *A61H 2201/50* (2013.01); *A61H 2201/5007* (2013.01); *A61H 2201/5061* (2013.01); *A61H 2201/5069* (2013.01); *A61H 2201/5071* (2013.01); *B60W 2710/08* (2013.01); *G05B 2219/40202* (2013.01); *G05B 2219/40305* (2013.01); *G05B 2219/45108* (2013.01); *G05B 2219/45109* (2013.01)

(56) References Cited

FOREIGN PATENT DOCUMENTS

| | | |
|---|---|---|
| JP | 2013-075042 A | 4/2013 |
| KR | 10-0623417 B1 | 9/2006 |
| KR | 10-0843311 B1 | 7/2008 |
| KR | 10-2012-0064571 A | 6/2012 |
| KR | 10-1171225 B1 | 8/2012 |

SYSTEM AND METHOD FOR CONTROLLING JOINT ANGLE OF KNEE-JOINT TYPE WALKING TRAINING ROBOT

TECHNICAL FIELD

The embodiment relates to a system and a method for controlling a joint angle of a knee-joint type walking training robot, and more particularly, to a system for controlling a joint angle of a knee-joint type walking training robot that estimates a gait phase of a walking rehabilitation patient and actively responds to the estimation according to a gait phase, and a method for controlling a joint angle of a knee-joint type walking training robot.

BACKGROUND ART

In recent years, due to the improvement of food lives and development of the medical technologies, the life spans of human beings have been prolonged and aged population has increased rapidly. It is most important for the aged to regularly exercise every day in order to maintain healthy lives for the rest of their lives. The aged persons who can move freely can do light exercises regularly while going to nearby mineral springs at daybreak every day or strolling around the villages. However, it is dangerous and difficult for the aged persons who cannot move freely due to the old ages or diseases to do exercise outdoor.

Further, for rehabilitation patients who cannot move well due to various industrial accidents, traffic accidents, or strokes, doing regular rehabilitation exercises for predetermined time periods every day are the best methods for recovering the previous heath states. Although a robot type walking exercise device that fixes a body to allow the user to do an upright walking exercise has been released, it is so high-priced to be purchased. Further, an exercise device that allows the aged or disabled or the rehabilitation patients to fix the body to the exercise device to safely do walking exercises.

The aged have functional differences due to the aging of the body functions as compared with the young. The functional differences include a body reaction time, a delay, degradation of cognitive skills, deterioration of sense of equilibrium. For this reason, the walking velocity, the step length, the walking frequency, the decrease of the joint motion range and the angular speed, and the sense of equilibrium of the aged are limited.

The abnormal walking of the aged is a main cause of hampering activities of daily living (ADL), and causes falls so that they become positive to social participation due to the fear of movement. Therefore, a walking rehabilitation of the aged is necessary to improve the quality of lift (QOL) of the aged.

In order to recover the walking functions of the aged, muscular forces should be maintained and improved through exercises. To achieve this, a suitable rehabilitation program should be established by recognizing the characteristics of the walking of the walkers, and a systematic and repetitive training should be executed through this. In order to perform rehabilitation training, assistant systems that the aged may rely on are widely used. The assistant systems may easily realize repetitive operations, and support the postures of patients instead, thereby increasing stability and training effects. Actually, the cases in which the rehabilitation using the assistant systems show effects in the upper aim rehabilitation treatments and the neural rehabilitation treatments, and the rehabilitation medical world have interests in treatments using the assistant systems.

An example of such technologies is disclosed in the following patent document and non-patent documents.

For example, Patent Document 1 (Korean Patent No. 10-0623417 (registered on Sep. 6, 2006)) discloses a walking assistant apparatus for old persons and rehabilitation patients including: a lower body having a plurality of legs installed on the left, right, front and rear sides thereof, and a horizontal frame connecting upper ends of the legs while being curved in a channel type a rear side of which is opened; an upper body having at least one pair of vertical frames arranged on the left and right sides and lower ends of which are coupled to opposite ends of the horizontal frame to be detachable from the horizontal frame and such that the heights thereof may be adjusted, and a plurality of connecting frames arranged on the left and right sides and connecting the front sides of the vertical frames corresponding to each other; and a safety fixing member connected to the upper body such that a walker may put on the safety fixing member, wherein the safety fixing member is detachably connected to the upper by four or more fixing members.

Further, Patent document 2 (Korean Unexamined Patent Publication No. 2012-0064571 (published on Jun. 19, 2012)) discloses a walking assistant robot control apparatus including a sensor unit configured to detect an input electromyogram and analyze the detected electromyogram signal, a signal generating unit configured to generates a walking signal according to a change degree of contraction of muscles through the analyzed electromyogram signal, and a control unit configured to control a walking assistant robot by using a walking signal.

Further, because the rehabilitation using a robot shows effective cases in the upper aim rehabilitation treatments and the neural rehabilitation treatments, the rehabilitation medical world having great interests in the treatment using robots. For example, the following non-patent document (J. Perry and J. Burnfield, Gait Analysis: Normal and Pathological Function, 2nd Edition, SLACK Incorporated, 2010.) discloses a technology of designing a controller configured to be operated according to the walking of the user for walking rehabilitation using a robot.

However, in the prior art, because it is difficult to accurately estimate the step length of a walker, it is impossible to drive the walking assistant device according to the walking of the walker. That is, it is important to perform a walking rehabilitation according to the walking of the walker, and according to the related art, it is impossible to control the assistant system according to the walking of the walker.

Further, the estimation of a joint angle of a knee-joint according to the related art includes a method using a pressure sensing resistor (FSR) on the bottom of a foot, a method using an angle or angular speed sensor (an inclination sensor, an acceleration sensor, or a gyro sensor), and a method using a vision system, but it is difficult to estimate a gate phase in a time series scheme.

DISCLOSURE

Technical Problem

It is an object of the disclosure to provide a system for controlling a joint angle of a knee-joint type walking training robot that can estimate a joint angle from a leg by using pressure sensors, and a system for controlling a joint angle of a knee-joint type walking training robot.

The present invention also provides a system for controlling a joint angle of a knee-joint type walking training robot that can list data of five pressure sensors in a time series scheme, estimates a movement time for walking and a length by which a sole of the foot makes contact with the ground surface, uses the estimated value in estimating an angle between the sole of the foot and the ground surface, conjectures a joint angle of a knee-joint to use the joint angle as a control parameter of a robot, and a system for controlling a joint angle of a knee-joint type walking training robot.

Technical Solution

In accordance with an aspect of the present invention, there is provided a system for controlling a joint angle of a knee-joint type walking training robot, the system including: a pressure measuring apparatus configured to measure a pressure of a foot sole of a walker by using a pressure sensor; and a joint angle estimating apparatus configured to estimate a joint angle of a knee-joint by extracting a movement time period for walking and a length of a part of the sole making contact with a ground surface based on the pressure of the foot sole measured by the pressure measuring apparatus.

The pressure measuring apparatus may include: a pressure measuring unit provided to correspond to the foot sole; and a transmission unit configured to transmit the pressure values measured by the pressure measuring unit to the joint angle estimating apparatus.

The joint angle estimating apparatus may include: a reception unit configured to receive the pressure values transmitted by the transmission unit; a pressure extracting unit configured to estimate a gait phase for the pressure values received in the reception unit; and a joint angle estimating unit configured to estimate the joint angle of the knee-joint during walking by estimating an angle between the foot sole and the ground surface according to the extraction value extracted by the pressure extracting unit.

The pressure extracting unit may extract a pressure according to the gait phase in a time series scheme.

The pressure measuring unit may include a plurality of pressure sensors sequentially arranged from the heel towards a big toe in response to a movement of a foot pressure during walking.

In accordance with another aspect of the present invention, there is provided a method for controlling a joint angle of a knee-joint type walking training robot, the method including: (a) detecting a pressure of a foot sole during walking by applying a plurality of sensors; (b) transmitting a pressure values detected in (a) to a pressure extracting unit; (c) extracting a walking velocity and a step length by the pressure extracting unit; (d) conjecturing an angle between the foot sole and a ground surface according to the extraction value extracted in (c); and (e) controlling a joint angle of the walking training robot according to the joint angle of the knee-joint during the walking conjectured in (d).

In (c), the walking velocity and the step length are extracted in a time series scheme by a plurality of pressure sensors sequentially arranged from a heel to a big toe in response to a movement of a foot pressure during walking.

(c) may be executed according to Equation 1.

$$Fi_{time} = \sum_{i=1}^{Timer_{max}} FST_{threshold} \times Dtime \quad \text{[Equation 1]}$$

wherein, $Fi_{time}$ denotes an FSR sensor that exceeds a time threshold value, $Timer_{max}$ denotes a timer period, $FSR_{threshold}$ denotes a value that is defined as '1' if the measurement value exceeds a threshold value, and $D_{time}$ is a sensor measurement period.

In (e), the joint angle of the knee-joint may be set as

Angle of knee-joint≈$Foot_{angle}$×1.5, in which $Foot_{angle}$ is an angle between the foot and the ground surface.

The $foot_{angle}$ between the foot and the ground surface may be set as $Foot_{angle}=\tan^{-1}(S1\_MD/(Foot\_length\times\alpha))$, in which S1_MD denotes a movement distance of the pressure sensor S1, Foot_length denotes a foot length (unit: cm) of the walker, and α denotes location constants (S1: 0, S2: 0.4, S3: 0.7, S4: 0.8, and S5: 1) of the pressure sensors.

Advantageous Effects

As described above, according to the system and method for controlling a joint angle of a knee-joint type walking training robot, a gait phase is estimated by realizing an apparatus for measuring a pressure of a foot, and a joint angle of a knee-joint type walking training robot can be easily controlled through a qualitative analysis of a correlation between the gait phase and the knee-joint.

Further, according to the system and method for controlling a joint angle of a knee-joint type walking training robot, control of a joint angle of a walking training robot can be easily applied to walking of a walking rehabilitation patient.

BEST MODE

Mode for Invention

The above or other objects and new features of the present invention will become clearer through the detailed description of the present invention and accompanying drawings.

Walking of a human being is classified into a stance phase and a swing phase. The stance phase occupies 60% of the gait phase and corresponds to a section in which the feet make contact with the ground surface. The swing phase occupies 40% of the gait phase, and corresponds to a section in which a foot is separated from the ground surface, swings, and then contacts the ground surface again.

Because the present invention may easily estimate the gait phases in time series according to an arrangement of pressure sensors, a method using pressure sensors (foot pressures) is applied to the classification of the gait phases.

Hereinafter, a configuration of the present invention will be described with reference to the accompanying drawings.

Figure 1:
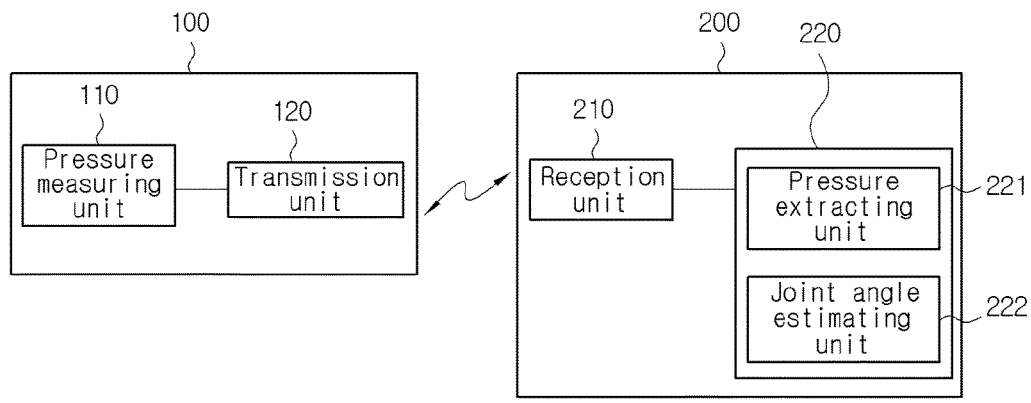
FIG. 1 is a block diagram of a system for controlling a joint angle of a knee-joint type walking training robot according to the present invention.
Figure 2:
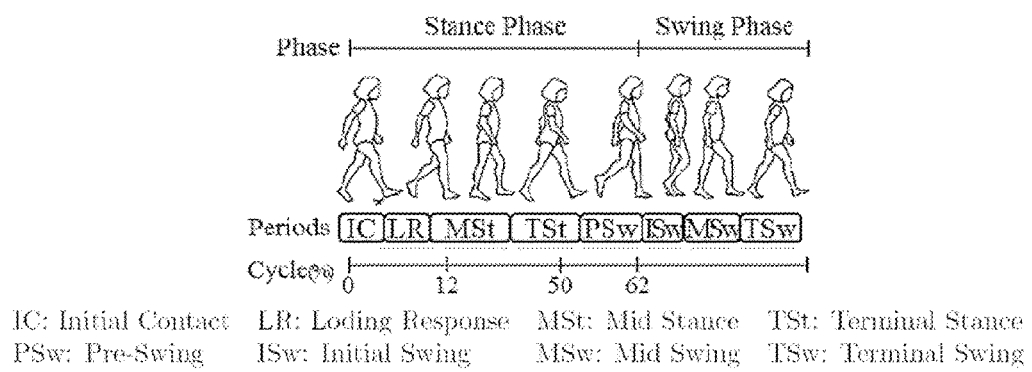
FIG. 2 is a view illustrating gait phases.
Figure 3:
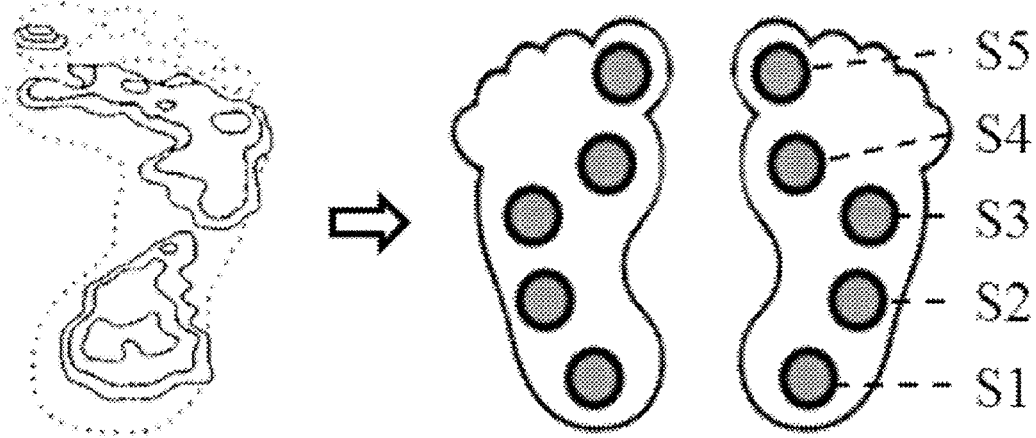
FIG. 3 is a view illustrating an arrangement of pressure sensors applied to control a joint angle of a knee-joint type walking training robot according to the present invention.

FIG. 1 is a block diagram of a system for controlling a joint angle of a knee-joint type walking training robot according to the present invention. FIG. 2 is a view illustrating gait phases. FIG. 3 is a view illustrating an arrangement of pressure sensors applied to control a joint angle of a knee-joint type walking training robot according to the present invention.

As illustrated in FIG. 1, the system for controlling a joint angle of a walking training robot according to the present invention is a system for controlling a joint angle of a knee-joint type walking training robot, and includes a pressure measuring apparatus 100 for measuring a pressure of the sole of the foot of a walker by using a pressure sensor, and a joint angle estimating apparatus 200 for estimating an joint angle of a knee-joint by extracting a walking movement time and a length by which the sole of the foot makes contact with the ground surface, based on the pressure of the sole of the foot measured by the pressure measuring apparatus 100.

The pressure measuring apparatus 100 includes a pressure measuring unit 110 provided to correspond to the sole of the foot, and a transmission unit 120 that transmits the pressure values measured by the pressure measuring unit 110 to the joint angle estimating apparatus 200.

As illustrated in FIG. 3, the pressure measuring unit 110 includes five pressure sensors S1, S2, S3, S4, and S5 that are sequentially disposed from the heel to the big toe in response to a movement of foot pressure during walking.

The sequentially disposed pressure sensors S1, S2, S3, S4, and S5 may be electrically capacitive pressure sensors, for example, using conductive fibers and provided in the form of an insole of a shoe.

The pressure sensors S1, S2, S3, S4, and S5 are sensors, a resistance value of which varies according to a change rate of a force applied to the sensors. Accordingly, gait phases may be sequentially estimated by properly disposing the sensors. The gait phases are as in FIG. 2. The timing when a foot makes contact with the ground surface is referred to as a stance phase, and because the foot pressures are sequentially moved from the heel strike to the forefoot strike of the foot, the gait phases may be sequentially estimated.

Accordingly, in the present invention, five pressure sensors S1, S2, S3, S4, and S5 are disposed as illustrated in FIG. 3 based on the distribution of foot pressures.

Further, it has been described that five sensors are provided as an example of the pressure sensors of FIG. 3, the present invention is not limited thereto, but the number of pressure sensors may be increased to allow the foot pressures to be measured more precisely.

The transmission unit 120 is electrically connected to the five pressure sensors S1, S2, S3, S4, and S5, and transmits the pressure values detected by the joint angle estimating apparatus 200 in a wired or wireless scheme. The transmission unit 120 may be provided on a side surface of the shoe worn by the walker such that the foot pressure of the walker is not applied to the transmission unit 120.

As illustrated in FIG. 1, the joint angle estimating apparatus 200 includes a reception unit 210 that receives the pressure values transmitted by the transmission unit and a joint angle estimating unit 220 that estimates a joint angle of the knee-joint according to the pressure values received by the reception unit 210.

The joint angle estimating unit 220 includes a pressure extracting unit 221 that estimates a gait phase according to the pressure values received by the reception unit 210 and a joint angle estimating unit 222 that estimates a joint angle of a knee-joint during walking by estimating an angle between the sole of the foot and the ground surface according to the estimation value extracted by the pressure extracting unit 221.

The pressure extracting unit 221 estimates a gait phase by measuring the values of the five pressure sensors S1, S2, S3, S4, and S5 as illustrated in FIG. 3 in a time division scheme.

Next, a method for controlling a joint angle of a knee-joint type walking training robot according to the present invention will be described with reference to FIGS. 4 to 9.

Figure 4:
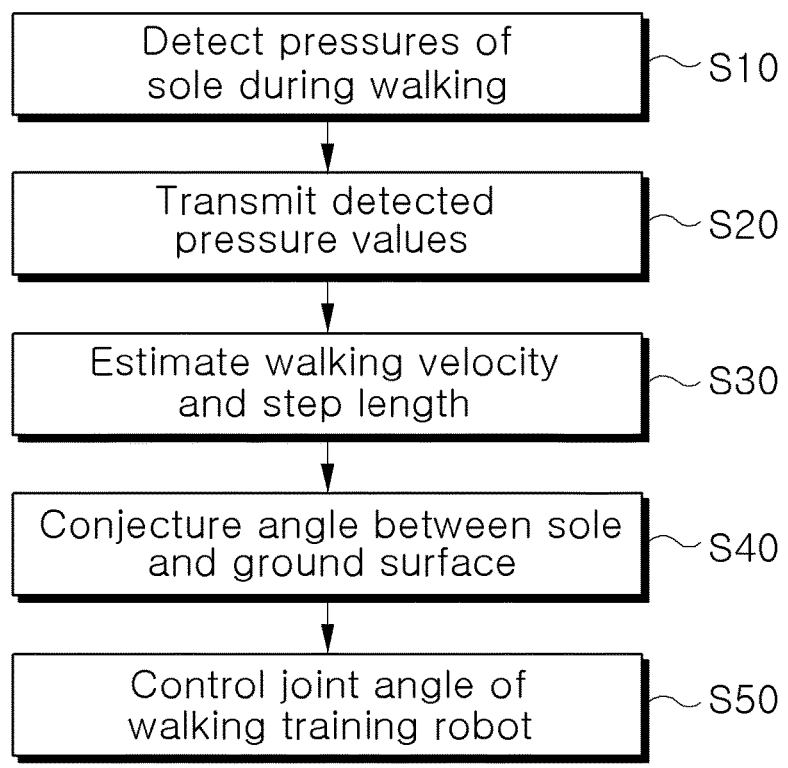
FIG. 4 is a flowchart of the system for controlling a joint angle of a knee-joint type walking training robot according to the present invention.
Figure 5:
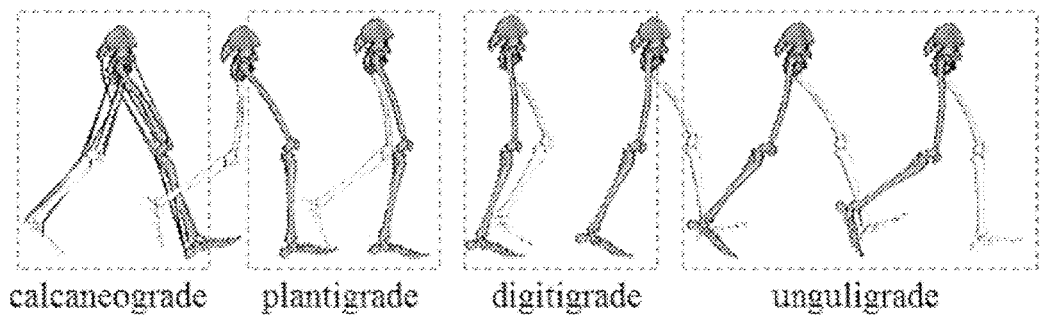
FIG. 5 is a view illustrating states in which walking of a human being is classified in stages.
Figure 6:
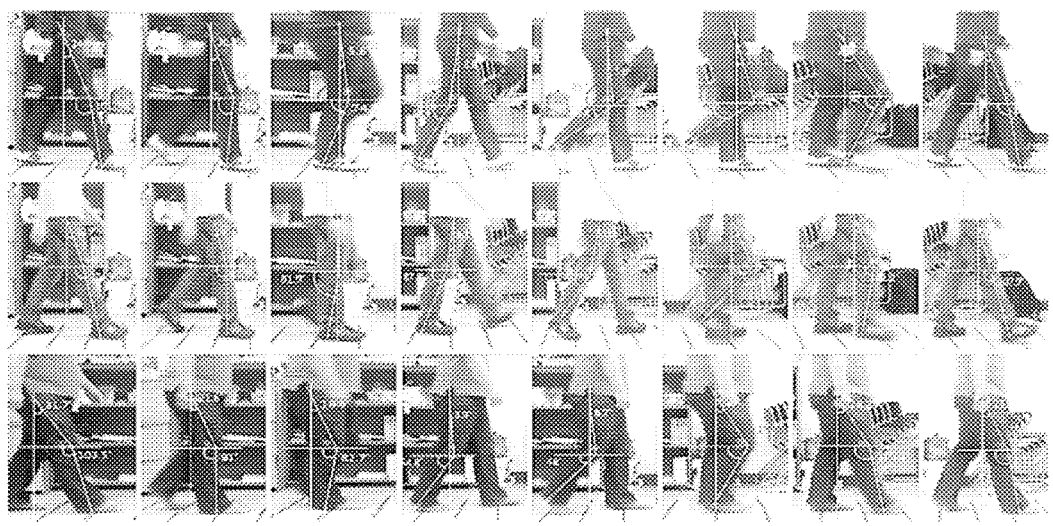
FIG. 6 is a view for filming and analyzing a plurality of general walking appearances in units of frames.
Figure 7:
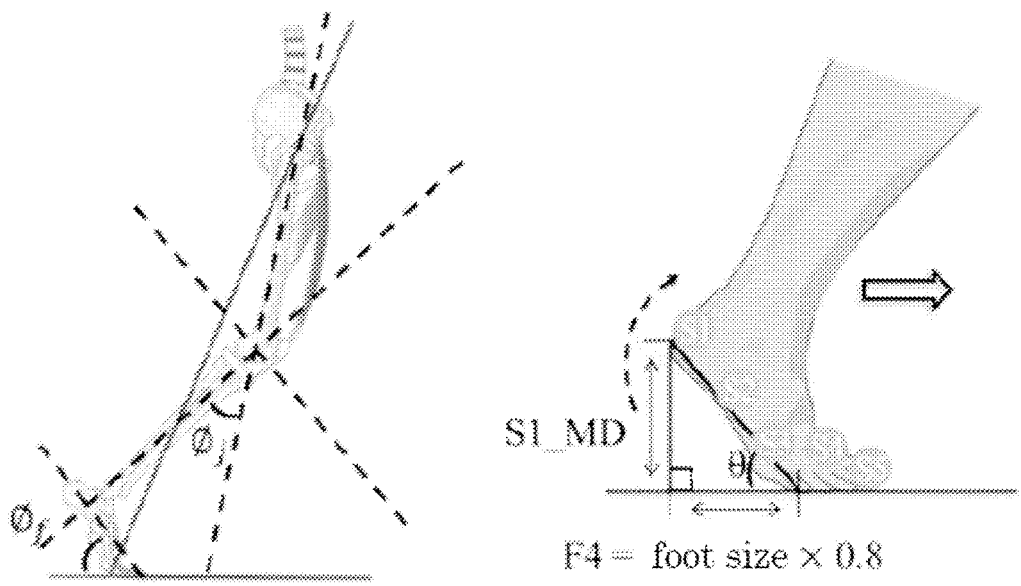
FIG. 7 is a view illustrating a relationship between an angle of the sole of the foot and a ground surface, and an angle of a knee-joint.
Figure 8:
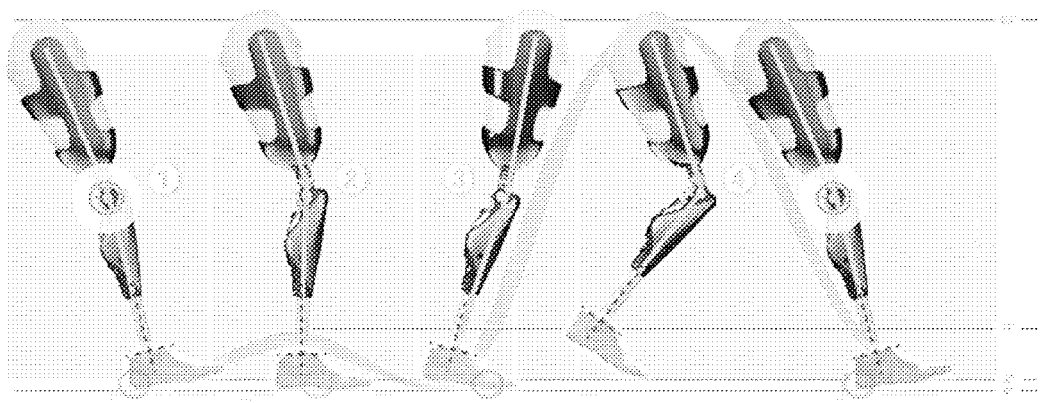
FIG. 8 is a view illustrating gait forms of a prosthetic leg.
Figure 9:
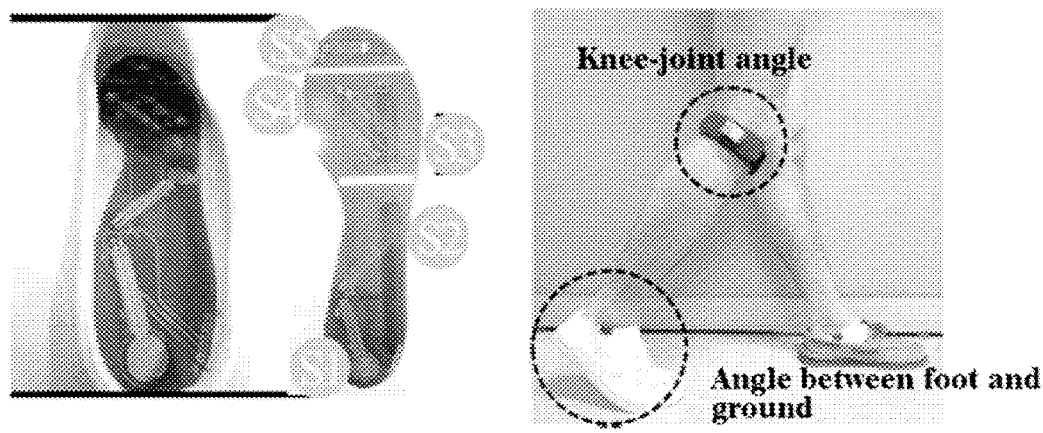
FIG. 9 illustrates diagrams of an apparatus for estimating a gait phase by mounting a pressure sensor of FIG. 3 on an insole.

FIG. 4 is a flowchart of the system for controlling a joint angle of a knee-joint type walking training robot according to the present invention. FIG. 5 is a view illustrating states in which walking of a human being is classified in stages. FIG. 6 is a view for photographing and analyzing a plurality of general walking appearances in units of frames. FIG. 7 is a view illustrating a relationship between an angle of the sole of the foot and a ground surface, and an angle of a knee-joint. FIG. 8 is a view illustrating gait forms of a prosthetic leg. FIG. 9 illustrates diagrams of an apparatus for estimating a gait phase by mounting a pressure sensor of FIG. 3 on an insole.

First, as illustrated in FIGS. 3 and 9A, for example, the five pressure sensors S1, S2, S3, S4, and S5 are provided in the insole of the shoe provided with the function of a flexible board. The five pressure sensors S1, S2, S3, S4, and S5 detect the pressures of the sole of the foot during walking (S10) The five pressure sensors S1, S2, S3, S4, and S5 are electrically connected to the transmission unit 120, and the transmission unit 120 transmits the pressure values detected by the five pressure sensors S1, S2, S3, S4, and S5 to the reception unit 120 (S20).

The present invention estimates the gait phase by measuring the values of the five pressure sensors S1, S2, S3, S4, and S5 in a time division scheme to detect a pressure change time of the foot pressure. A method for estimating a walking velocity and a step length is as in Equation 1.

If the pressure change times of the five pressure sensors S1, S2, S3, S4, and S5 are measured through the method, the gait phase may be estimated, and because the time (t) for which the foot makes contact with the ground surface and the length of the foot may be known, the walking velocity and step length may be estimated.

$$Fi_{time} = \sum_{i=1}^{Timer_{max}} FST_{threshold} \times Dtime \qquad [\text{Equation 1}]$$

wherein, $Fi_{time}$ denotes an FSR sensor that exceeds a time threshold value, $Timer_{max}$ denotes a timer period, $FSR_{threshold}$ denotes a value that is defined as '1' if the measurement value exceeds a threshold value, and $D_{time}$ is a sensor measurement period.

Next, a method for controlling a joint angle of a knee-joint type walking assisting robot based on the gait phase estimated in the above-described manner.

The stance phase of a human being may be classified into four grades in consideration of the behaviors of animals, and as illustrated in FIG. 5, is classified into 'calcaneo grade'→'plantu grade'→'digi grade'→'unguli grade' in Latin.

The skeleton structure of a human being is not mechanically imperfect, and thus the unstable skeleton structure is complemented by muscles. For the reason, the present invention performs a qualitative analysis of a correlation of the gait phase and the knee-joint, prior to a quantitative analysis. The qualitative analysis was deduced by photographing walking of a plurality of persons in videos as in FIG. 6 and combining a frame analysis method and walking of a human being analyzed by Perry.

It can be seen form the deduction result that an angle between the sole of the foot and the ground surface when the 'digi grade' of the stance phase starts, is two times as large as an angle of the knee-joint as illustrated in FIG. 7.

Accordingly, the present invention provides a method for controlling the angle of the knee-joint based on information of the stance phase of walking.

The method is expressed according to Equations 2 to 5.

$$W\_S = \text{Foot\_length}/(F5'_{time} - F1'_{time}) \quad [\text{Equation 2}]$$

wherein W_S denotes a walking velocity, $F5'_{time}$ denotes a time period for which the pressure sensor S5 makes contact with the ground surface in FIGS. 3 and 7, $F1'_{time}$ denotes a time period for which the pressure sensor S1 makes contact with the ground surface in FIGS. 3 and 7, and Foot_length denotes a length (unit:* cm) of the foot of the walker.

$$S1\_MD = W\_S \times (F?'_{time} - F1'_{time}) \quad [\text{Equation 3}]$$

wherein S1_MD denotes a movement distance of the pressure sensor S1, W_S denotes a walking velocity, $F?'_{time}$ denotes a time period for which the pressure sensors S2 to S5 are separated from the ground surface in FIGS. 3 to 7, and $F1'_{time}$ denotes a time period for which the pressure sensor S1 is separated from the ground surface in FIGS. 3 and 7.

$$\text{Foot}_{angle} = \tan^{-1}(S1_{MD}/(\text{Foot}_{length} \times \alpha)) \quad [\text{Equation 4}]$$

wherein $\text{Foot}_{angle}$ denotes an angle between the foot and the ground surface, S1_MD denotes a movement distance of the pressure sensor S1, Foot_length denotes a foot length (unit: cm) of the walker, and α denotes the location constants (S1: 0, S2: 0.4, S3: 0.7, S4: 0.8, and S5: 1) of the pressure sensors.

$$\text{Angle of knee-joint} \approx \text{Foot}_{angle} \times 1.5 \quad [\text{Equation 5}]$$

In Equations 2 to 5, the premise is that the ankle and the foot form the right angle of 90°.

As described above, in the method of controlling an angle of a knee-joint according to the present invention, the walking velocity may be estimated because the foot length of the person for the measurement may be known by measuring a time for a pressure change of the pressure sensors S1 and S5 illustrated in FIG. 3 while the walking progresses from 'calcaneo grade' to 'plantu grade'. Further, the time period for which the sole of the foot is separated from the ground surface may be measured as the walking progresses from 'plantu grade' to 'digi grade', the angle between the sole of the foot and the ground surface is estimated according to the correlation with the estimated walking velocity.

The angle inferred in step S40 is substituted in Equation 5 for estimating the angle of the knee-joint.

Because of the premise that the ankle and the foot always forms 90### if the walking progresses based on the conjectured joint angle, it is expected that the walking seems that a lower limb amputee walks while wearing a prosthetic leg as illustrated in FIG. 8.

Accordingly, normal walking is made possible through walking training by allowing the walking training robot to smoothly move with an ankle. That is, the joint angle of the walking training robot may be controlled according to the present invention (S50).

The following experiments were performed to realize the present invention.

The experiment will be described with reference to FIGS. 9 to 12.

Figure 10:
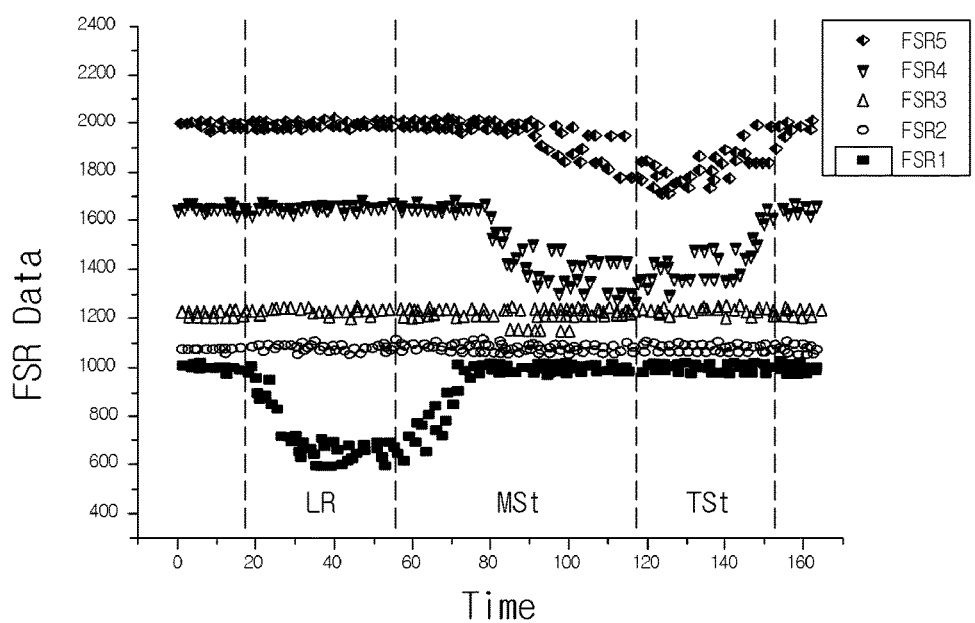
FIG. 10 is a graph depicting a measurement state of the pressure sensor according to the present invention.
Figure 11:
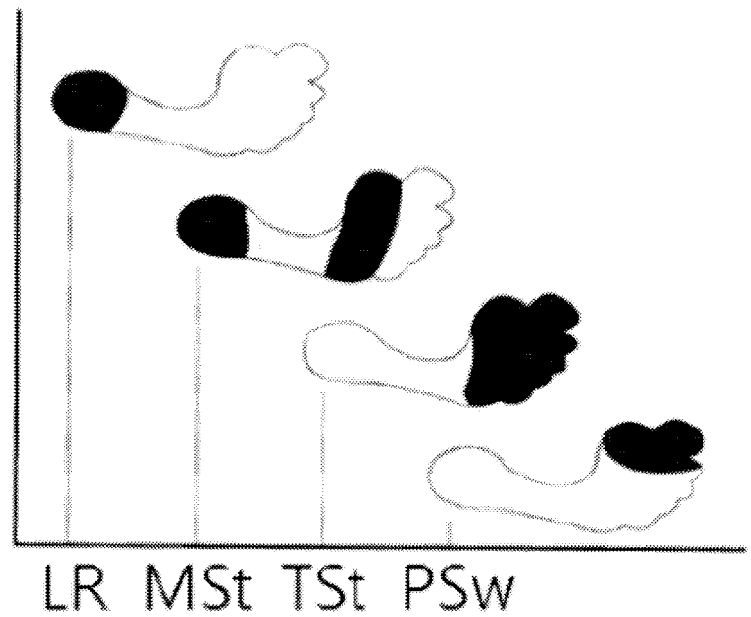
FIG. 11 is a view illustrating a support pattern of a foot.
Figure 12:
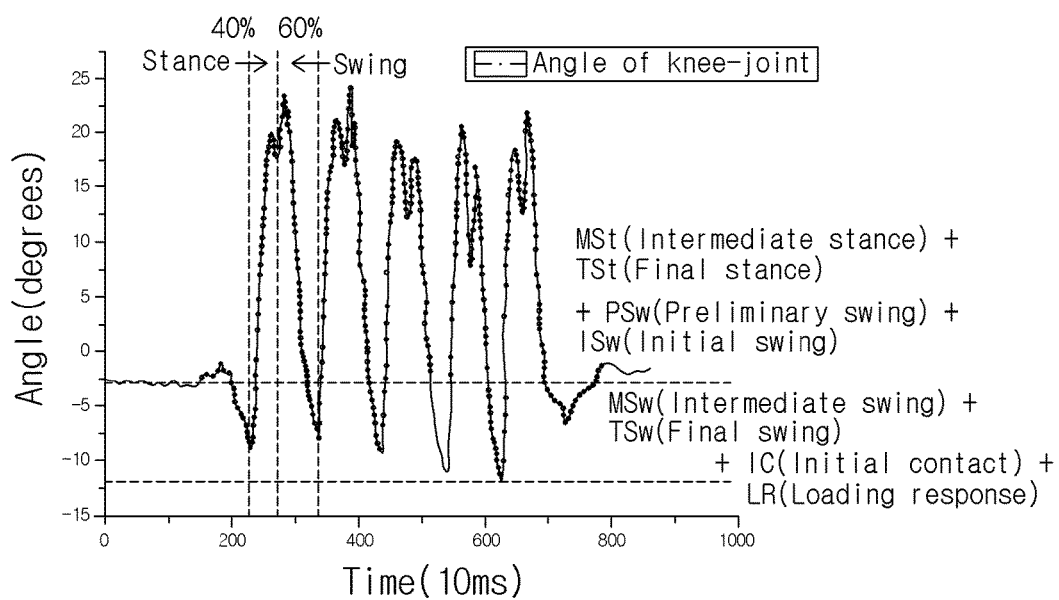
FIG. 12 is a graph depicting the angles of a knee-joint according to the present invention.

FIG. 10 is a graph depicting a measurement state of the pressure sensor according to the present invention. FIG. 11 is a view illustrating a support pattern of a foot. FIG. 12 is a graph depicting the angles of a knee-joint according to the present invention.

The experimental method estimates a gait phase by applying the arrangement of the pressure sensors of FIG. 3 to an insole of a shoe. Further, in order to verify whether the joint angle of the knee-joint robot estimated through Equation 2-5 coincides with an actual angle of the knee-joint to a degree, a comparison/verification was made by attaching an inertial sensor for measuring an angle of a knee as illustrated in FIG. 9B.

FIG. 9A illustrates a pressure measuring apparatus applied to an insole of a shoe based on FIG. 3.

FIG. 10 is a graph depicting an actually measured gait phase. The foot pressure of a human being studied earlier by Perry shows difference sizes of pressure according to the curves of the sole of the foot as illustrated in FIG. 11. Accordingly, when FIGS. 10 and 11 are compared, it is determined that the foot pressure measured in the present invention was properly measured.

The coincidence rate of the joint angle of the knee-joint robot according to the present invention and the actual joint angle of a knee-joint was identified.

In order to measure the joint angle of the knee-joint, a joint angle was measured by attaching the inertia sensor to the knee as illustrated in FIG. 9B. The coincidence rate of the measurement result and the estimation of a joint angle suggested by the present invention are shown in Table 1.

TABLE 1

|   | Calculation | Sensor | Ratio |
|---|---|---|---|
| 1 | 18.5° | 20.3° | 91% |
| 2 | 19.4° | 22.2° | 87% |
| 3 | 21.2° | 18.5° | 114% |
| 4 | 19.8° | 21.2° | 93% |
| 5 | 20.6° | 17.8° | 115% |
| Total | — | — | 89% |

An error between the joint angle measured by the inertia sensor of FIG. 9B and the joint angle estimated according to the present invention was ±2.80°, and the coincidence rate thereof was 89%. Because the error is different to a degree according to the walking pattern of persons, it can be seen that the method according to the present invention is a meaningful method.

The present invention suggests a method for estimating a joint angle to control a joint angle of a knee-joint robot based on a gait phase. To achieve this, a gait phase was estimated by realizing an apparatus for measuring a pressure of a foot and a correlation between a gait phase and a knee-joint was qualitatively analyzed. As a result, it was identified that an angle between the sole of the foot and the ground surface is about two times as large as the joint angle of the knee-joint in a plantu grade>digi grade section. The assumption was verified through an experiment and a coincidence rate of ±89% was shown as compared with an actual joint angle. The value verifies that the method suggested by the present invention may be a meaningful method.

Although the invention made by the present inventor has been described in detail according to the embodiment, the present invention is not limited to the embodiment and it is understood that various modifications may be made without departing from the essence of the present invention.

A joint angle of a knee-joint type walking training robot can be easily controlled by using the system and the method for controlling a joint angle of a knee-joint type walking training robot according to the present invention.

The invention claimed is:

1. A system for controlling a joint angle of a knee-joint type walking training robot, the system comprising:
   a pressure measuring apparatus configured to measure a pressure of a sole of a foot of a walker by using a pressure sensor; and
   a joint angle estimating apparatus configured to estimate a joint angle of a knee-joint by extracting a movement time period for walking and a length by which the foot sole makes contact with a ground surface based on the pressure of the foot sole measured by the pressure measuring apparatus,
   wherein the joint angle estimating apparatus comprises:
   a receiver for receiving pressure values transmitted by a transmitter;
   a pressure extracting circuit configured to estimate a gait phase for the received pressure values; and
   a joint angle estimating circuit configured to estimate the joint angle of the knee-joint during walking by estimating an angle between the foot sole and the ground surface according to the gait phase estimated by the pressure extracting circuit.

2. The system of claim 1, wherein the pressure measuring apparatus comprises:
   a pressure measuring unit provided to correspond to the foot sole; and
   the transmitter configured to transmit the pressure values measured by the pressure measuring unit to the joint angle estimating apparatus.

3. The system of claim 2, wherein the pressure measuring unit comprises a plurality of pressure sensors sequentially arranged from a heel towards a big toe.

4. The system of claim 3, wherein the pressure extracting circuit extracts a pressure according to the gait phase in a time series scheme.

5. A method for controlling a joint angle of a knee-joint type walking training robot, the method comprising the steps of:
   (a) detecting a pressure of a foot sole during walking by applying a plurality of sensors;
   (b) transmitting pressure values detected in step (a) to a pressure extracting circuit;
   (c) extracting a walking velocity and a step length by the pressure extracting circuit;
   (d) conjecturing an angle between the foot sole and a ground surface according to the walking velocity and step length extracted in step (c); and
   (e) controlling the joint angle of the walking training robot according to the angle between the foot sole and the ground surface conjectured in step (d).

6. The method of claim 5, wherein in step (c), the walking velocity and the step length are extracted in a time series scheme by the plurality of pressure sensors sequentially arranged from a heel to a big toe.

7. The method of claim 5, wherein step (c) is executed according to Equation 1:

$$Fi_{time} = \sum_{i=1}^{Timer_{max}} FST_{threshold} \times Dtime, \qquad \text{[Equation 1]}$$

wherein $Fi_{time}$ denotes an FSR sensor that exceeds a time threshold value, $Timer_{max}$ denotes a timer period, $FSR_{threshold}$ denotes a value that is defined as '1' if a measurement value exceeds a threshold value, and $D_{time}$ is a sensor measurement period.

8. The method of claim 5, wherein in step (e), the joint angle of the knee-joint is set as $Foot_{angle} \times 1.5$,
   in which $Foot_{angle}$ is the angle between the foot sole and the ground surface.

9. The method of claim 8, wherein the $Foot_{angle}$ between the foot sole and the ground surface is set as $\tan^{-1}(S1\_MD/(Foot\_length \times \alpha))$,
   in which $S1\_MD$ denotes a movement distance of a first pressure sensor, $Foot\_length$ denotes a foot length of a walker, and $\alpha$ denotes location constants of the plurality of pressure sensors, wherein $\alpha$ is 0 for the first pressure sensor, 0.4 for a second pressure sensor, 0.7 for a third pressures sensor, 0.8 for a fourth pressure sensor, and 1 for a fifth pressure sensor.

* * * * *